(12) United States Patent
Pacetti et al.

(10) Patent No.: US 9,364,350 B2
(45) Date of Patent: Jun. 14, 2016

(54) STENT WITH EASED CORNER FEATURE

(71) Applicant: Abbott Cardiovascular Systems Inc., Santa Clara, CA (US)

(72) Inventors: Stephen D. Pacetti, San Jose, CA (US); Richard Rapoza, San Francisco, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 13/937,984

(22) Filed: Jul. 9, 2013

(65) Prior Publication Data

US 2015/0018935 A1 Jan. 15, 2015

(51) Int. Cl.
*A61F 2/82* (2013.01)
*A61F 2/89* (2013.01)
*A61F 2/915* (2013.01)

(52) U.S. Cl.
CPC ... *A61F 2/82* (2013.01); *A61F 2/89* (2013.01); *A61F 2/915* (2013.01); *A61F 2230/0054* (2013.01); *Y10T 29/49995* (2015.01)

(58) Field of Classification Search
CPC ... A61F 2/89; A61F 2/915; A61F 2250/0014; A61F 2250/0026; A61F 2250/0036–2250/0039; A61F 2/82
See application file for complete search history.

(56) References Cited

U.S. PATENT DOCUMENTS

| | | | |
|---|---|---|---|
| 4,733,665 A | 3/1988 | Palmaz | |
| 4,800,882 A | 1/1989 | Gianturco | |
| 4,886,062 A | 12/1989 | Wiktor | |
| 5,514,154 A | 5/1996 | Lau et al. | |
| 5,569,295 A | 10/1996 | Lam | |
| 6,475,233 B2 * | 11/2002 | Trozera | 623/1.15 |
| 8,002,817 B2 | 8/2011 | Limon | |
| 8,303,644 B2 | 11/2012 | Lord et al. | |
| 8,323,760 B2 | 12/2012 | Zheng et al. | |
| 8,388,673 B2 | 3/2013 | Yang et al. | |
| 2003/0187498 A1* | 10/2003 | Bishop | 623/1.16 |
| 2004/0133265 A1* | 7/2004 | Duffy | 623/1.16 |
| 2010/0244305 A1 | 9/2010 | Contiliano et al. | |
| 2010/0256737 A1 | 10/2010 | Pollock et al. | |
| 2013/0085563 A1 | 4/2013 | Stankus et al. | |

FOREIGN PATENT DOCUMENTS

| | | |
|---|---|---|
| WO | WO 03/022180 A1 | 3/2003 |
| WO | WO 2005/060873 A1 | 7/2005 |

OTHER PUBLICATIONS

International Search Report and Written Opinion for PCT/US2014/044638, mailed Oct. 23, 2014, 10 pgs.
Angioplasty Summit Abstracts/Oral, The Am. J. of Cardiology, Apr. 23-26, 2013, p. 23B.
Bosiers et al., "Coronary and endovascular applications of the Absorb™ bioresorbable vascular scaffold", Interv. Cardiol. 4(6), pp. 621-631 (2012).
Miller "Abbott's Bioresorbable Stent Shows Durable Results in Absorb Trial", The Gray Sheet, pp. 17-18, Mar. 2003.

* cited by examiner

*Primary Examiner* — Howie Matthews
(74) *Attorney, Agent, or Firm* — Squire Patton Boggs (US) LLP

(57) ABSTRACT

An implantable stent includes a plurality of rings. At least a distal end ring has an eased corner feature formed in the polymer substrate at a radially outward, distal-facing corner of the ring while relatively sharp corners of the polymer substrate are maintained in radially inward corners of the ring.

14 Claims, 7 Drawing Sheets

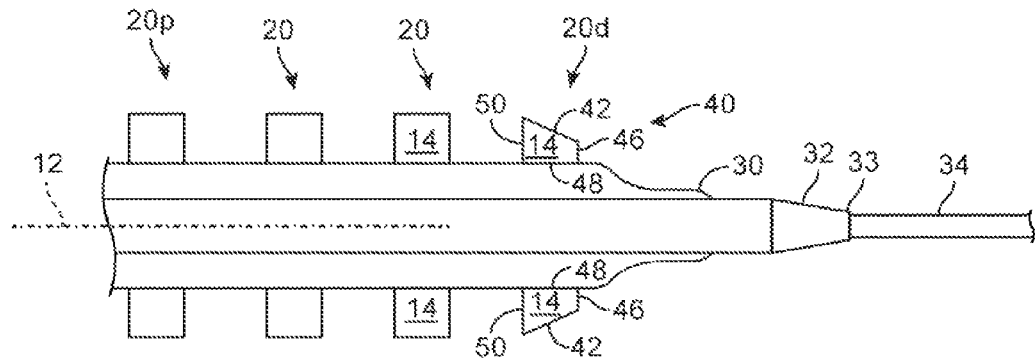
FIG. 9
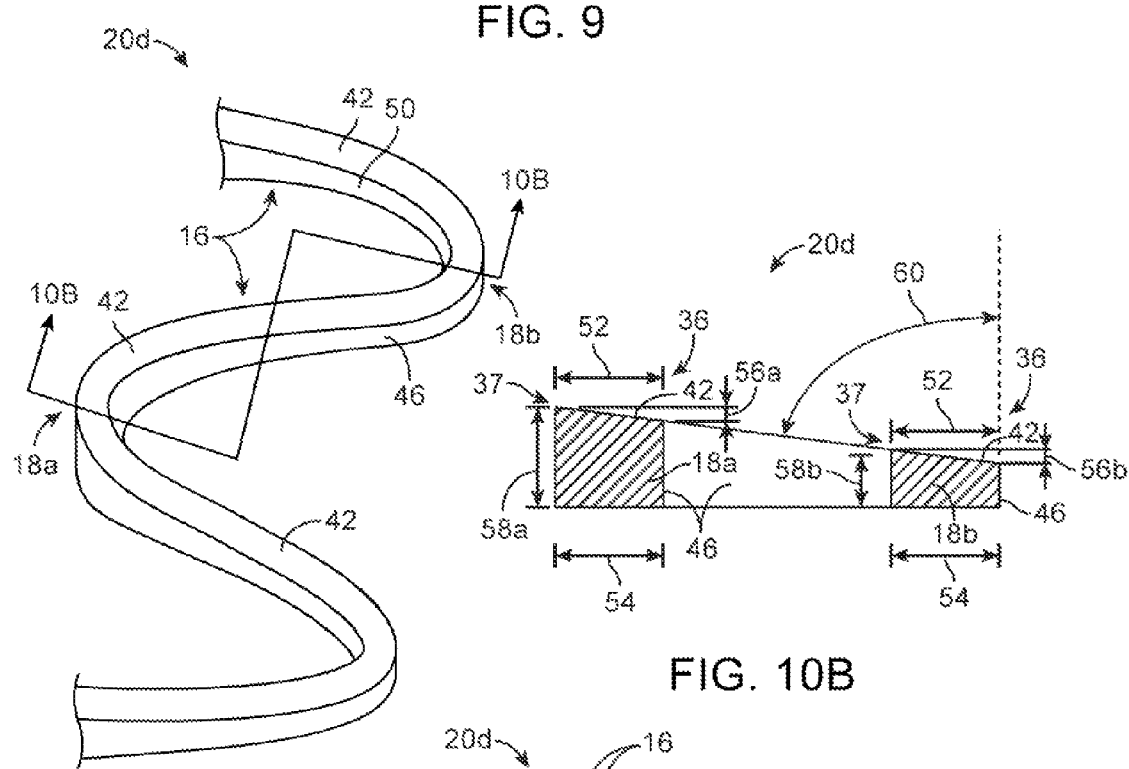
FIG. 10A
FIG. 10B
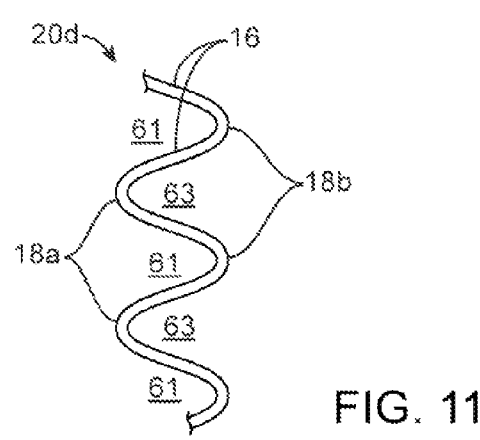
FIG. 11

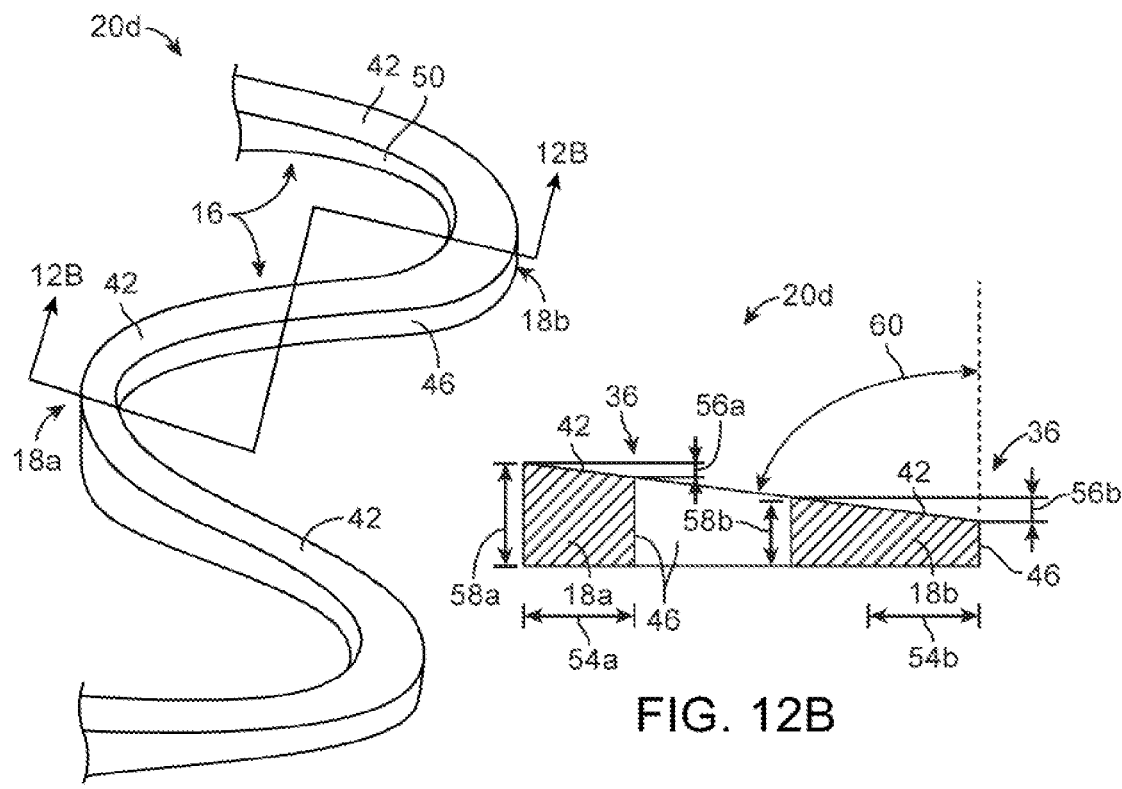
FIG. 12A
FIG. 12B
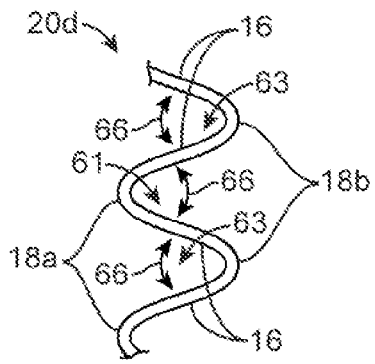
FIG. 13
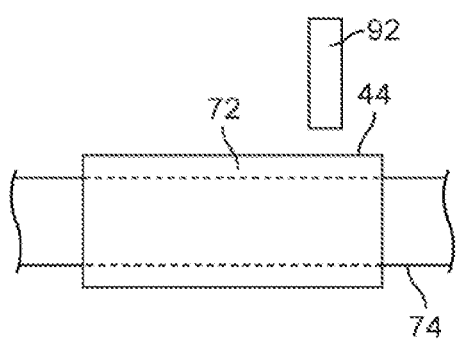
FIG. 14A
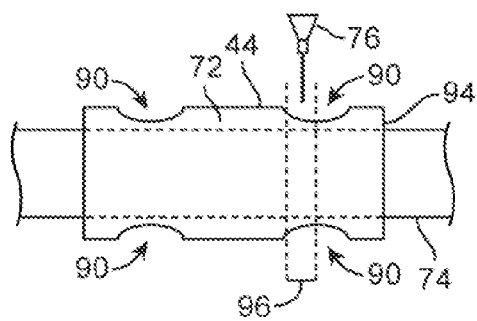
FIG. 14B

STENT WITH EASED CORNER FEATURE

FIELD OF THE INVENTION

This invention relates generally to implantable medical devices and, more particularly, to polymeric stents.

BACKGROUND OF THE INVENTION

Stents are frequently used in the medical field to open vessels affected by conditions such as stenosis, thrombosis, restenosis, vulnerable plaque, and formation of intimal flaps or torn arterial linings caused by percutaneous transluminal coronary angioplasty (PCTA). Stents are used not only as a mechanical intervention, but also as vehicles for providing biological therapy. As a mechanical intervention, stents act as scaffoldings, functioning to physically hold open and, if desired, to expand a vessel wall. Stents may be capable of being compressed in diameter, so that they can be moved through small vessels with the use of a catheter or balloon-catheter, and then expanded to a larger diameter once they are at the target location. Examples of such stents include those described in U.S. Pat. No. 4,733,665 to Palmaz, U.S. Pat. No. 4,800,882 to Gianturco, U.S. Pat. No. 4,886,062 to Wiktor, U.S. Pat. No. 5,514,154 to Lau et al., and U.S. Pat. No. 5,569,295 to Lam.

A stent must have sufficient radial strength to withstand structural loads, such as radial compressive forces, imposed on the stent as it supports the walls of a vessel or other anatomical lumen. In addition, the stent must possess sufficient flexibility to allow for crimping, deployment, and cyclic loading from surrounding tissue. Also, a sufficiently low profile, that includes diameter and size of struts, is important. As the profile of a stent decreases, the easier is its delivery through an anatomical lumen, and the smaller the disruption in the flow of blood or other bodily fluid.

Stents made of bioresorbable polymers have been developed to allow for improved healing of the anatomical lumen. Examples of bioresorbable polymer stents include those described in U.S. Pat. No. 8,002,817 to Limon, U.S. Pat. No. 8,303,644 to Lord, and U.S. Pat. No. 8,388,673 to Yang. FIG. 1 shows an end segment of an exemplary bioabsorbable polymer stent 10 designed to be delivered through anatomical lumen using a catheter and subsequently expanded. Stent 10 has a cylindrical shape having central axis 12 and includes a pattern of interconnecting structural elements or struts 14. Axis 12 extends through the center of the cylindrical shape formed by struts 14. The stresses involved during compression and deployment are generally distributed throughout various struts 14 but are focused at the bending elements or strut junctions.

There are different types of struts 14. Struts 14 include a series of ring struts 16 that are connected to each other by bending elements 18. Ring struts 16 and bending elements 18 form sinusoidal rings 20 configured to be reduced and expanded in diameter. Rings 20 are arranged longitudinally and centered on axis 12. Struts 14 also include link struts 22 that connect rings 20 to each other. Rings 20 and link struts 22 collectively form a tubular scaffold of stent 10. Ring 20d is located the distal end of stent 10.

Bending elements 18 form a more acute angle when stent 10 is crimped to allow radial compression of stent 10 in preparation for delivery through an anatomical lumen. Bending elements 18 subsequently bend to form a larger angle when stent 10 is deployed to allow for radial expansion of stent 10 within the anatomical lumen. After deployment, stent 10 is subjected to static and cyclic compressive loads from surrounding tissue. Rings 20 are configured to maintain the expanded state of stent 10 after deployment.

Polymer stents are typically more flexible than metallic stents. While greater flexibility facilitates deliverability through tortuous anatomical lumen, flexibility of the polymer substrate material also requires individual struts of polymer stents to be thicker than struts of comparable metallic stents in order to meet requisite mechanical strength requirements. Thicker struts can result in a polymer stent having a larger stent scaffold profile, or outer diameter, during delivery through an anatomical lumen.

In some cases, calcification can be present on the interior surface of an anatomical lumen. Due to a larger stent scaffold profile and higher conformability of the scaffold against the walls of the anatomical lumen, sharp edges of polymer stent struts may catch on spicules of calcium present in the anatomical lumen. However, making stent struts thinner in an effort to reduce the chance of catching calcium on anatomical lumen walls, can impact the mechanical strength of the stent.

Accordingly, there is a continuing need for stent strut configurations and manufacturing methods that facilitate delivery of polymer stents.

SUMMARY OF THE INVENTION

Briefly and in general terms, the present invention is directed to an implantable stent and a method for making an implantable stent.

In aspects of the present invention, an implantable stent comprises a first ring and a second ring, each of the first ring and the second ring made of a polymer substrate material forming a strut abluminal surface, a strut luminal surface, a distal-facing strut side surface, and a proximal-facing strut side surface. The distal-facing strut side surfaces meet strut luminal surfaces to form sharp radially inward corners on the first ring and the second ring, an eased corner feature is formed in the polymer substrate material of the first ring, and the eased corner feature is located at a radially outward, distal-facing corner of the first ring and is configured to ease movement of the first ring through an anatomical lumen.

In aspects of the present invention, a method comprises providing a tubular construct made of a polymer substrate material, and removing polymer substrate material from the tubular construct to form a first ring and a second ring. The removing of the polymer substrate material includes forming sharp radially inward corners on the first ring and the second ring, and forming an eased corner feature at a radially outward, distal-facing corner of the first ring.

Any one or a combination of two or more of the following can be appended to the above aspects of the invention to form additional aspects of the invention.

The eased corner feature has an eased width and an eased depth, the eased width is at least 5% of strut width, and the eased depth is at least 5% of strut height.

The first ring is a distal end ring.

An eased corner feature is formed in the polymer substrate material of the second ring and is configured to ease movement of the second ring through an anatomical lumen.

The eased corner feature of the second ring is located on a radially-outward, distal-facing corner of the second ring.

The eased corner feature of the second ring is located on a radially-outward, proximal-facing corner of the second ring.

The first ring is a distal end ring, and second ring is a proximal end ring.

A third ring is disposed between the first ring and the second ring, the third ring configured to radially expand and made of a polymer substrate material forming a strut abluminal surface, a strut luminal surface, a distal-facing strut side surface, and a proximal-facing strut side surface, wherein the distal-facing strut side surface and proximal-facing strut side surface meet the abluminal surface to form sharp radially outward corners on the third ring.

A plurality of additional rings each of which made of the polymer substrate material, wherein an eased corner feature is formed in the polymer substrate material at radially outward, distal-facing corner of each of the additional rings, and the eased corner feature is configured to ease movement of each of the rings through an anatomical lumen.

The first ring includes ring struts joined together by a proximal bending element and a distal bending element, wherein the ring struts, the proximal bending element, and the distal bending element form a sinusoidal shape, wherein a width ratio is a ratio of eased width of the eased corner feature to strut width, and the width ratio of the first ring is the same at the proximal bending element and at the distal bending element, and an eased depth of the eased corner feature of the first ring is the same at the proximal bending element and at the distal bending element.

The eased width at the proximal bending element and at the distal bending element is less than 100% of strut width.

The eased width at the proximal bending element and at the distal bending element is 100% of strut width.

Strut height is greater at the proximal bending element than at the distal bending element, and the strut width is the same at the proximal bending element and at the distal bending element.

Strut height is greater at the proximal bending element than at the distal bending element, and the strut width is less at the proximal bending element than at the distal bending element to allow for uniform expansion of the first ring.

The eased corner feature of the first ring includes a flat surface oriented at a bevel angle less than 90 degrees relative to the distal-facing strut side surface.

The eased corner feature of the first ring includes a convex surface.

Sharpness of a radially outward, proximal-facing corner of the first ring is maintained during forming of the eased corner feature at the radially outward, distal-facing corner of the first ring.

Forming of the sharp radially inward corners and forming of the eased corner feature are performed using the same cutting tool.

Forming of the sharp radially inward corners and the forming of the eased corner feature are performed using different cutting tools.

The cutting tool used to form the eased corner feature is selected from the group consisting of a laser, a water jet, a knife, a buffing wheel, a jet of abrasive material, and a combination of two or more thereof.

Forming of the eased corner feature includes removing polymer substrate material from the tubular construct using the cutting tool.

Forming of the eased corner feature includes removing polymer substrate material from the tubular construct using a thinning tool followed by using the cutting tool.

Forming of the sharp radially inward corners is performed using a first tool, and is followed by the forming of the eased corner feature using a second tool.

The features and advantages of the invention will be more readily understood from the following detailed description which should be read in conjunction with the accompanying drawings.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

BRIEF DESCRIPTION OF THE DRAWINGS

FIG. 9 is a cross-section view of a polymer stent mounted on a catheter, showing an eased corner feature on a distal end ring of the stent.

FIG. 10A is a perspective view showing the distal end ring of FIG. 9 before the distal end ring is crimped onto a balloon catheter.

FIG. 10B is a cross-section view along line 10B-10B in FIG. 10A.

FIG. 11 is a flattened, plan view of a portion of the distal end ring of FIG. 10A after radial expansion of the distal end ring during implantation of the stent.

FIG. 12A is a perspective view of a distal end ring.

FIG. 12B is a cross-section view along line 12B-12B in FIG. 12A.

FIG. 13 is a flattened, plan view of a portion of the distal end ring of FIG. 12A after radial expansion of the distal end ring during implantation of the stent.

FIGS. 14A and 14B are elevation views, showing a process for forming the eased corner feature according to FIGS. 9-13.

DETAILED DESCRIPTION OF EXEMPLARY EMBODIMENTS

As used herein, a "stent" is a device that is placed inside the body of a person or animal and, more particularly, within an anatomical lumen or cavity. Examples of anatomical lumen and cavities in which a stent can be placed include without limitation arterial or venous vasculature, urethra, ureter, fallopian tubes, esophagus, and the like. Non-limiting examples of stents within the scope of the present invention are those which are self-expanding and balloon expandable, and which are configured for percutaneous transluminal delivery methods. Stents which have a finite lifetime in vivo are sometimes referred to as scaffolds due to their temporary nature.

As used herein, "bioresorbable" refers to a material capable being completely eroded, degraded (either biodegraded and/or chemically degraded), and/or absorbed when exposed to bodily fluids (such as blood or other fluid); and can be gradually resorbed, absorbed and/or eliminated by the body. Other terms such as biodegradable, bioabsorbable, and bioerodible may be found in the literature and while these terms have specific definitions, they are often used interchangeably.

As used herein, "biostable" refers to a material that is not bioresorbable.

As used herein, "abluminal surface" refers to a radially outward facing surface.

As used herein, "luminal surface" refers to a radially inward facing surface.

A used herein, "side surface" refers to a surface which is disposed between and which connects an abluminal surface and a luminal surface.

The word "distal" when used in the context of a device, refers to a portion of the device located at the front of the device or which faces in a forward direction during typical use of the device. The word "proximal" when used in the context of a device, refers to a portion of the device located at the rear of the device or which faces in a rearward direction during typical use of the device.

Figure 1:
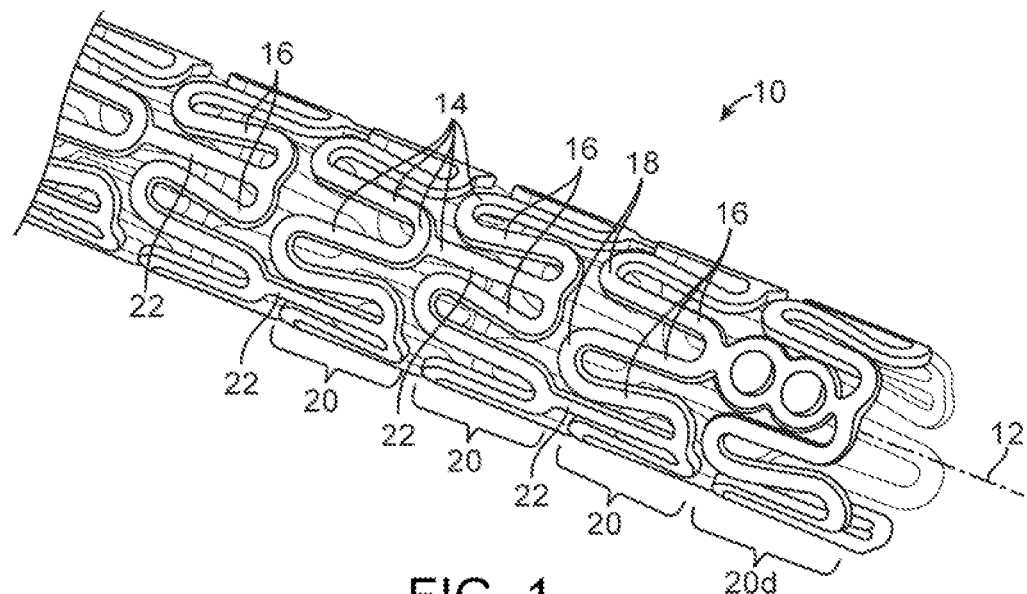
FIG. 1 is a perspective view of a polymer stent.
Figure 2:
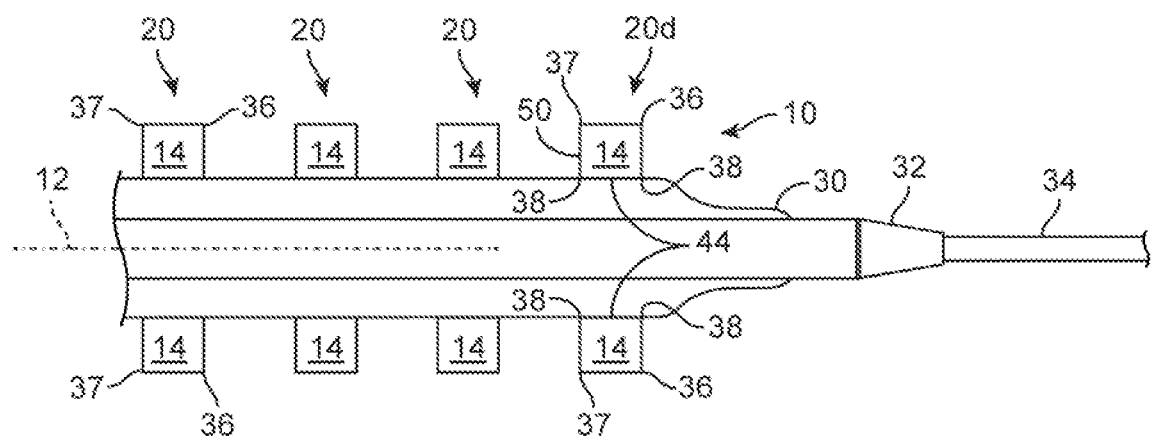
FIG. 2 is a cross-section view of a polymer stent, showing the stent mounted on a catheter.

Referring now in more detail to the exemplary drawings for purposes of illustrating embodiments of the invention, wherein like reference numerals designate corresponding or like elements among the several views, there is shown in FIG. 2a cross-section view of exemplary polymer stent 10 crimped onto folded balloon 30 of catheter 32 being tracked on guidewire 34. Stent struts 14 have the same height and width. Also, each stent strut 14 has sharp corners 36, 37, 38. Stent 10 has no eased corner feature.

As used herein, "eased corner feature" is a feature that blunts or dulls a corner on a ring to ease movement of the ring through an anatomical lumen.

Figure 3:
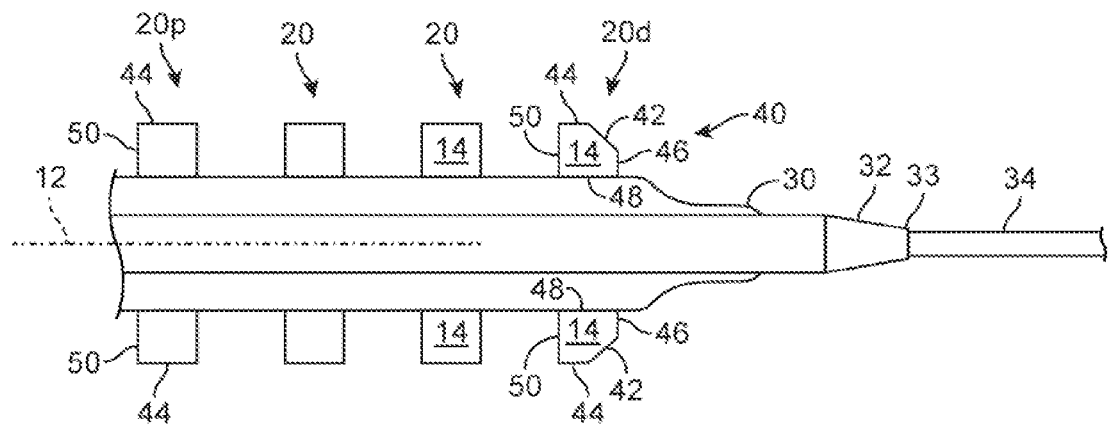
FIG. 3 is a cross-section view of a polymer stent mounted on a catheter, showing an eased corner feature on a distal end ring of the stent.
Figure 4A:
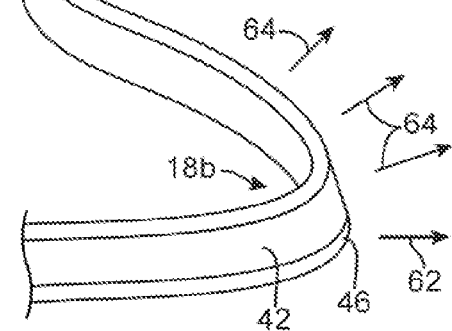
FIG. 4A is a perspective view showing the distal end ring of FIG. 3 before the distal end ring is crimped onto a balloon catheter.
Figure 4B:
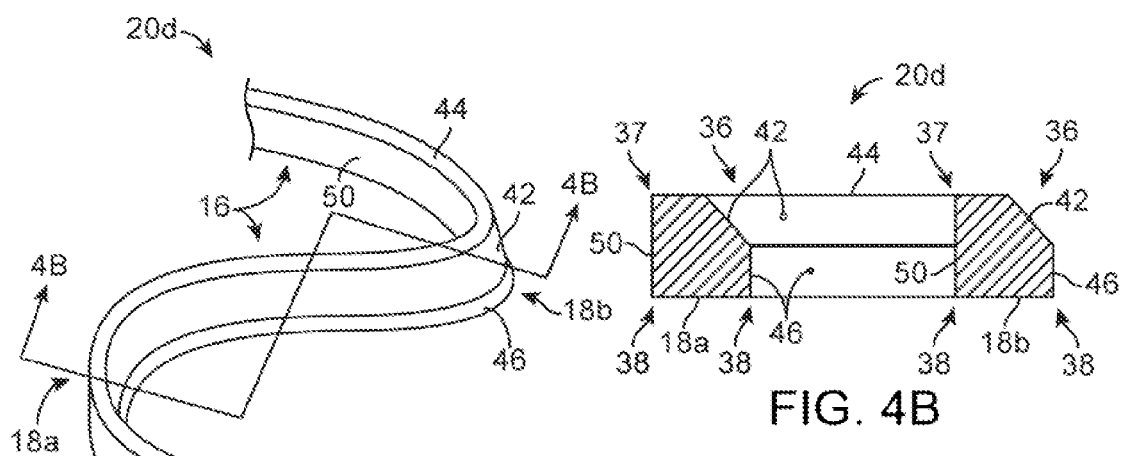
FIG. 4B is a cross-section view along line 4B-4B in FIG. 4A.
Figure 5:
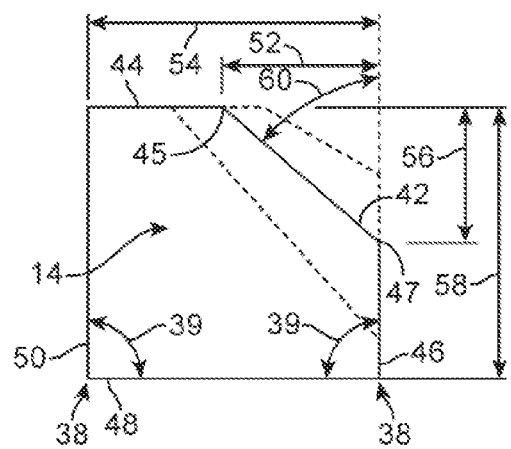
FIG. 5 is a cross-section view of a stent strut, showing a bevel-type eased corner feature.

FIGS. 3-5 show exemplary stent 40 having struts 14 with eased corner feature 42. Eased corner feature 42 enables stent 40 to move easily past deposits, such as calcium, on the inner surface of an anatomical lumen. Eased corner feature 42 is in the form of a bevel, also referred to as a chamfer, connecting strut abluminal surface 44 and distal-facing strut side surface 46.

As used herein, "distal-facing" refers to a direction toward forward tip 33 of catheter 32 on which the stent is mounted or to an orientation facing in a forward or distal direction when the stent is being advanced through an anatomical lumen. The phrase "proximal-facing" refers to a direction away from forward tip 33 of catheter 32 on which the stent is mounted or to an orientation facing in a rearward direction when the stent is being pushed forward through an anatomical lumen.

Referring again to FIG. 3, stent 40 has multiple rings 20 which include proximal end ring 20p and distal end ring 20d. Distal end ring 20d is shown with eased corner feature 42 at strut abluminal surface 44 and distal-facing strut side surface 46. There is no eased corner feature at strut luminal surface 48 and proximal-facing strut side surface 50 of distal end ring 20d.

Only distal end ring 20d has eased corner feature 42. Eased corner feature 42 is absent from all other rings 20p, 20 on stent 40. Having eased corner feature 42 on only distal end ring 20d minimizes any impact on radial strength that eased corner feature 42 may have on the stent.

In other embodiments, both distal and proximal end rings have eased corner feature 42. For proximal end ring 20p, eased corner feature 42 would be present at strut abluminal surface 44 and proximal-facing strut side surface 50. Eased corner feature 42 would be absent from strut luminal surface 48 and distal-facing strut side surface 46 of proximal end ring 20p. Having eased corner feature 42 on proximal end ring 20p can facilitate backward movement of stent 40 past deposits, such as calcium, on the inner surface of an anatomical lumen. This can occur in situations where the stent cannot be advanced to the target lesion and the delivery system with stent must be removed. Having eased corner feature 42 on only proximal and distal end rings 20p, 20d allows for maximization of radial strength at the stent medial segment between the proximal and distal end rings.

As shown in FIGS. 4A and 4B, eased corner feature 42 follows the three-dimensional sinusoidal shape of distal end ring 20d. FIG. 4B shows a cross-section view of distal end ring 20d taken across bending elements 18a, 18b at the troughs and peaks between ring struts 16. Eased corner feature 42 is at radially outward, distal-facing corner 36 of ring 20d. Radially outward, distal-facing corner 36 is the corner between distal-facing strut side surface 46 and strut abluminal surface 44.

In other embodiments, eased corner feature 42 would also follow the three-dimensional sinusoidal shape of proximal end ring 20p in the same manner as shown in FIGS. 4A and 4B except eased corner feature 42 would be located at radially outward, proximal-facing corner 37. Radially outward, proximal-facing corner 37 is the corner between proximal-facing strut side surface 50 and strut abluminal surface 44.

In FIG. 5, eased width 52 of eased corner feature 42 is one-half strut width 54. As used herein, "strut width" of a particular strut is a dimension from distal-facing strut side surface 46 to proximal-facing strut side surface 50, as measured in a direction normal to any of the distal- and proximal-facing strut side surfaces 46, 50. Eased width 52 is measured along the same line as strut width 54 and is the distance from the extreme distal edge 47 of the eased corner feature to the extreme proximal edge 45 of the eased corner feature. Eased width 52 can be from 1% to 100% of strut width 54. Width ratio is the ratio of eased width 52 to strut width 54. The width ratio can be at least 5%, at least 10%, at least 25%, at least 50% or at least 75%. In some embodiments, strut width 54 is between 50 microns and 250 microns. For example, eased width 52 can be 96 microns while strut width 54 can be 191 microns. Other dimensions are possible.

Eased depth 56 of eased corner feature 42 is one-half strut height 58. As used herein, "strut height" of a particular strut is a dimension from the strut abluminal surface 44 to the strut luminal surface 48, as measured in a direction normal to any of the abluminal and strut luminal surfaces 44, 48. Eased depth 56 is measured along the same line as strut height 58 and is the distance from the extreme distal edge 47 of the eased corner feature to the extreme proximal edge 45 of the eased corner feature. Eased depth 56 can be from 1% to 100% of the strut height 58. Eased depth 56 can be at least 5%, at least 10%, at least 25%, at least 50%, or at least 75% of strut height 58. In some embodiments, strut height 58 is between 50 microns and 250 microns. Other dimensions are possible.

Bevel angle 60 of eased corner feature 42 is forty-five degrees. As used herein, "bevel angle" is the angle of incidence measured from a first imaginary line on a flat surface of eased corner feature 42 to a second imaginary line perpendicular to luminal surface 48. Furthermore, the first and second imaginary lines define an imaginary plane normal to any of the distal- and proximal-facing strut side surfaces 46, 50. Bevel angle 60 can be any non-zero angle from 5 degrees to 85 degrees, more narrowly from 10 degrees to 80 degrees, more narrowly from 20 degrees to 70 degrees, and more narrowly from 30 degrees to 60 degrees. Other ranges for bevel angle 60 are possible.

The broken lines in FIG. 5 show two non-limiting examples in which eased corner feature 42 is configured with different eased widths 52, different eased depths 56, and different bevel angles 60.

Figure 6:
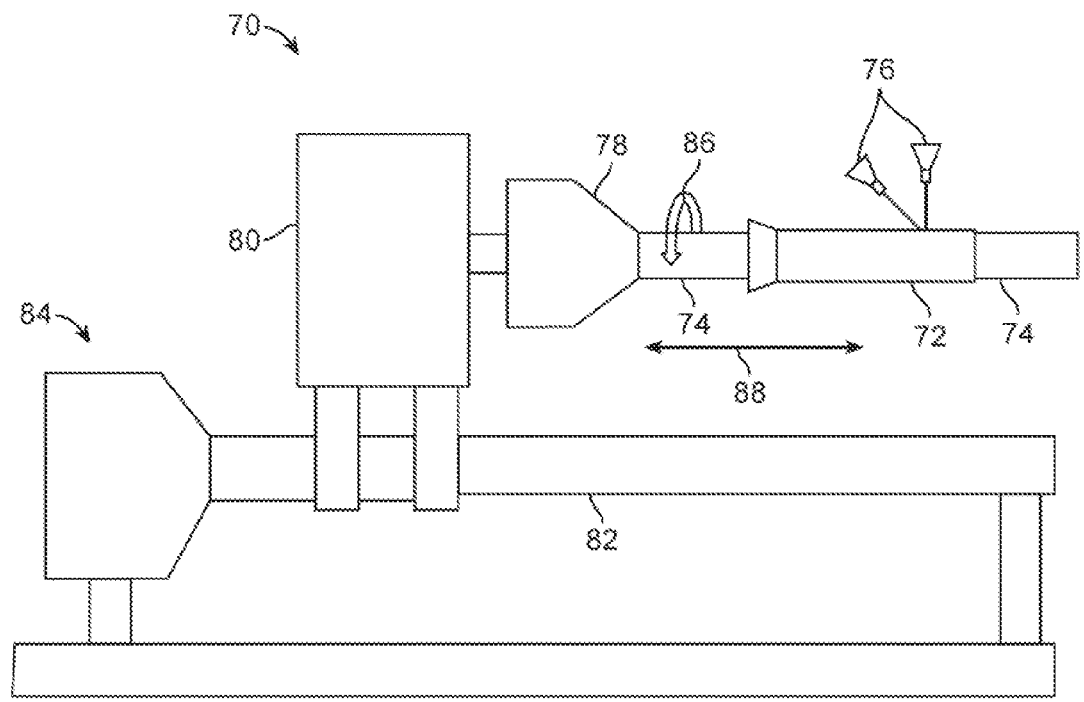
FIG. 6 is an elevation view of an apparatus for fabricating a stent, showing a cutting tool for forming an eased corner feature.

FIG. 6 shows apparatus 70 for making stent 40. Tubular construct 72 is carried on cylindrical mandrel 74 which passes through the center of tubular construct 72. Mandrel 74 is removably mounted via holder 78 to motor 80. Motor 80 is movably mounted on linear rail 82 of translational stage 84. Tubular construct 72 can be a polymer tube from which stent struts 14 will be cut, or tubular construct 72 can be a stent scaffold which already has stent struts 14. Cutting tool 76 can be a water jet, blade, or laser. A cutting tool 76 is used to make cuts into tubular construct 72 to form eased corner feature 42. For example, cutting tool 76 can be used to form eased corner feature 42 on either distal-facing side surface 46 or proximal-facing side surface 50 that was formed previously by another cutting tool. Alternatively, cutting tool 76 can also be used to form all three distal-facing side surface 46, proximal-facing side surface 50, and eased corner feature 42.

Apparatus 70 is configured to move tubular construct 72 and cutting tool 76 relative to each other to allow cuts that follow any desired stent strut pattern. Relative motion includes a combination of rotational motion 86 and axial translation 88. Rotational motion 86 is accomplished by rotation of mandrel 74 by motor 80. Axial translation 88 is accomplished by sliding mandrel 74 together with motor 80 on rail 82. An electronic controller is coupled to motor 80 and translational stage 84 to precisely control the relative motion, and is coupled to cutting tool 76 to lower and lift a water jet or blade or to activate or deactivate a laser device at the appropriate time.

Figures 7, 8:
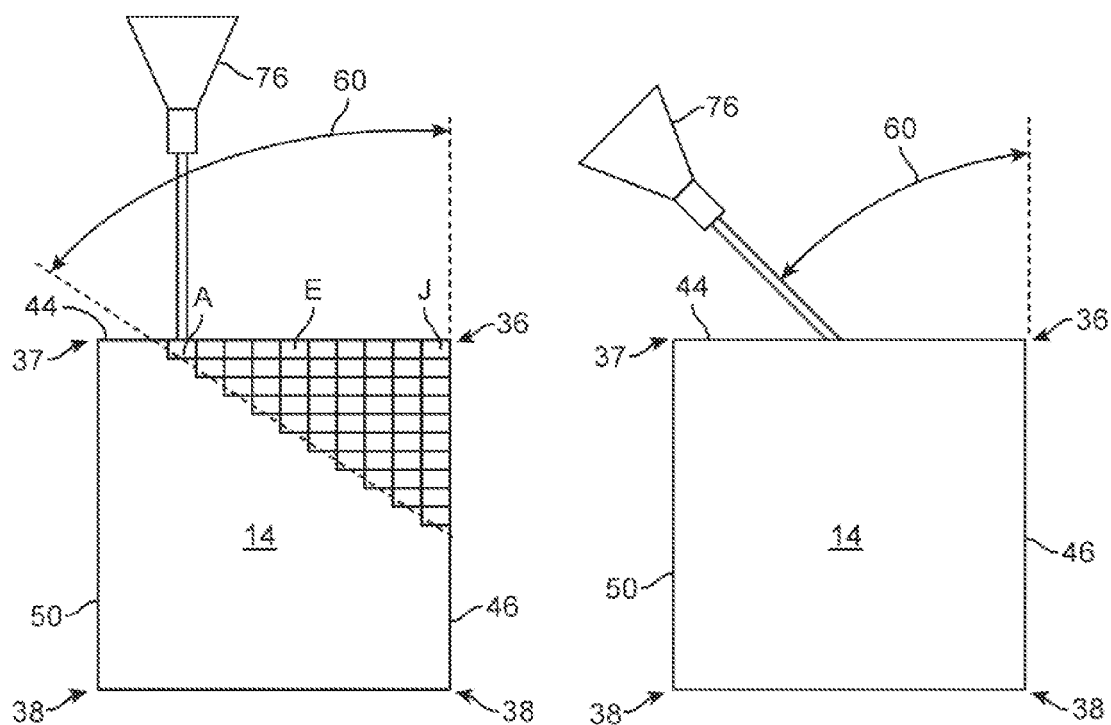
FIG. 7 is a cross-section view of a stent strut, showing a laser beam perpendicular to the stent strut abluminal surface.
FIG. 8 is a cross-section view of a stent strut, showing a laser beam at an oblique angle to the stent strut abluminal surface.

In FIG. 7, cutting tool 76 is in the form of a laser device configured to apply beam pulses to incrementally ablate and remove polymer substrate material from stent strut 14. The laser beam could be directed perpendicularly to abluminal surface 44 as illustrated. A bevel or other shape of eased corner feature 42 is created by varying the number of pulses as a function of position of the laser beam relative to any of distal- and proximal-facing strut side surfaces 46, 50. The small rectangles in FIG. 7 can represent the number of pulses for each axial position of the laser beam. As the beam moves axially to the right in FIG. 7, the number of pulses increases to create a deeper cut. For example, with laser beam at position A, only one pulse may be used to create a shallow cut. With laser beam at position E, five pulses may be used to create a deeper cut. With laser beam at position J, ten pulses may be used to create an even deeper cut. Multiple cuts of varying depth can create any desired shape.

In FIG. 8, cutting tool 76 is in the form of a laser device configured to direct a beam at an oblique angle corresponding to bevel angle 60 (FIG. 5). As indicated above, "bevel angle" is the angle between two lines on an imaginary plane normal to any of distal- and proximal-facing strut side surface 46, 50. However, the orientation of strut side surfaces 46, 50 of any sinusoidal ring will change along the circumference of the ring, as shown in FIG. 4A. For example, distal-facing strut side surface 46 may face distally (in the direction of arrow 62 in FIG. 4A) at peaks and troughs of bending elements 18 and face in other directions (arrows 64) at ring segments between bending elements 18. Therefore, to maintain the same bevel angle throughout ring 20d, it will be necessary to have a degree of relative motion in addition to rotational motion 86 and axial translation 88 (FIG. 6). For example, during rotational motion 86 and axial translation 88, cutting tool 76 can be pivoted relative to tubular construct 72 so that the imaginary plane of bevel angle 60 remains perpendicular or normal to distal-facing strut side surface 46. Maintaining the same bevel angle would help maintain the same cross-sectional area throughout the ring and, thereby, minimize variation in mechanical strength among various parts of the ring.

In FIGS. 7 and 8, polymer substrate material is removed only from radially outward, distal-facing corner 36 to form eased corner geometry 42 on distal end ring 20d or another ring 20, 20p. No material is removed from radially outward, proximal-facing corner 37 and radially inward corners 38.

In other embodiments, polymer substrate material is removed only from radially outward, proximal-facing corner 37 to form eased corner geometry 42 on proximal end ring 20p or another ring 20, 20d. No material is removed from radially outward, distal-facing corner 36 and radially inward corners 38.

In FIGS. 9-13, eased corner feature 42 is in the form of a bevel. Eased width 52 (e.g., FIG. 10B) is 100% of strut width 54. Consequently, eased corner feature 42 forms the entirety of the strut abluminal surface. Eased corner feature 42 is illustrated on distal end ring 20d. Eased corner feature 42 is located on radially outward, distal-facing corner 36 since eased depth 56 is on distal-facing strut side surface 46.

Eased corner feature 42 of can be implemented on only distal end ring 20d as illustrated, or on both distal and proximal end rings 20d, 20p. Having eased corner feature 42 present on only distal end ring 20d or only distal and proximal end rings 20d, 20p provides advantages described above for FIGS. 3-4B. For embodiments in which eased corner feature 42 is implemented on proximal end ring 20p, descriptions below in reference to distal end ring 20d would similarly apply except eased corner feature 42 would be located on radially outward, proximal-facing corner 37.

In FIGS. 9-10B, the strut cross-sectional area is not maintained the same throughout end ring 20d. The cross-sectional area is illustrated by diagonal hatching in FIG. 10B.

FIGS. 10A and 10B show how eased corner feature 42 follows the three-dimensional sinusoidal shape of distal end ring 20d. FIG. 10B shows a cross-section view of distal end ring 20d taken across bending elements 18a, 18b at the troughs and peaks between ring struts 16. Bending elements 18a, 18b have equal strut widths 54, equal eased widths 52, equal eased depths 56, and equal bevel angles 60. Eased depths 56a and 56b are the same in terms of distance, although the ratio of eased depth 56a to strut height 58a at proximal bending element 18a is less than the ratio of eased depth 56b to strut height 58b at distal bending element 18b. Proximal bending element 18a has strut height 58a greater than strut height 58b of distal bending element 18b, which results in a difference in cross-sectional area.

In some embodiments, the cross-sectional area of distal end ring 20d varies continuously from a maximum cross-sectional area at proximal bending element 18a to a minimum cross-sectional area at distal bending element 18b. Strut height varies continuously from a maximum strut height 58a at proximal bending element 18a to a minimum strut height 58b at distal bending element 18b.

In some embodiments, the variation in cross-sectional area may correspond to a variation in area moment of inertia and mechanical strength among various segments of ring 20*d*. Segments near proximal bending element 18*a* can have a greater area moment of inertia and thereby be less flexible than segments near distal bending element 18*b*, which may have a lower area moment of inertia. This variation can, in some embodiments, result in non-uniform expansion of ring 20*d* during implantation, as shown in FIG. 11. With non-uniform expansion, there are large empty spaces 61 and small empty spaces 63 between ring struts 16. With uniform expansion, empty spaces 61, 63 would be equal.

Uniformity in the size of empty spaces 61, 63 between ring struts 16 may be desired to improve support of surrounding tissue after implantation and provide for uniform stresses amongst bending elements 18*a*, 18*b*. Such uniformity may be accomplished, as shown in FIGS. 12A and 12B, by increasing strut width 54 at distal bending element 18*b* to compensate for its smaller strut height 58 and, thereby, increase the area moment of inertia at distal bending element 18*b* from that in FIG. 10B.

FIGS. 12A and 12B show how eased corner feature 42 follows the three-dimensional sinusoidal shape of distal end ring 20*d*. FIG. 12B shows a cross-section view of distal end ring 20*d* taken across bending elements 18*a*, 18*b* at the troughs and peaks between ring struts 16. Bending elements 18*a*, 18*b* have equal bevel angles 60. Proximal bending element 18*a* has strut height 58*a* greater than strut height 58*b* of distal bending element 18*b*. To compensate for its smaller strut height, distal bending element 18*b* has strut width 54*b* greater than strut width 54*a* of proximal bending element 18*a*.

In some embodiments, the cross-sectional shape of ring 20*d* varies continuously from proximal bending element 18*a* to distal bending element 18*b*. The cross-sectional shape is the perimeter of the area illustrated by diagonal hatching in FIG. 12B. Strut height 58 decreases continuously from a maximum strut height 58*a* at proximal bending element 18*a* to a minimum strut height 58*b* at distal bending element 18*b*. Strut width 54 increases continuously from a minimum strut width 54*a* at proximal bending element 18*a* to a maximum strut width 54*b* at distal bending element 18*b*.

The variation in strut height 58 and strut width 54 described above, in combination with eased corner feature 42, can allow for increased uniformity in the size of empty spaces between ring struts 16 after expansion of stent 40 during implantation, as shown in FIG. 13. In some embodiments, strut height 58 decreases continuously from a maximum strut height 58*a* at proximal bending element 18*a* to a minimum strut height 58*b* at distal bending element 18*b*, and strut width 54 increases continuously from a minimum strut width 54*a* at proximal bending element 18*a* to a maximum strut width 54*b* at distal bending element 18*b*, such that angles 66 between one pair of ring struts 16 is the same as that for another pair of ring struts 16 on ring 20*d*. The size of empty spaces 61, 63 may also be uniform.

The bevel-type eased corner feature 42 of FIGS. 9-13 can be fabricated by thinning a portion of tubular construct 72 and then forming any of proximal and distal end rings 20*p*, 20*d* on thinned portion 90.

As used herein, "bevel-type eased corner feature" includes one or more surfaces each defined by a bevel angle. The surfaces can be smooth or have some irregularities, such as the step-wise profile shown in the highly enlarged illustration in FIG. 7. For example, bevel-type eased corner feature can include a first surface having a bevel angle of 60 degrees and a second surface having a bevel angle of 30 degrees. Strut abluminal surface 44 would connect to the first surface, which would connect to the second surface, which would connect to distal-facing strut side surface 46.

As shown in FIG. 14A, abluminal surface 44 of tubular construct 72 is machined with thinning tool 92. Tubular construct 72 is mounted on mandrel 74 of the apparatus shown in FIG. 6 to enable relative movement between thinning tool 92 and tubular construct 72. Thinning tool 92 modifies abluminal surface 44 to form thinned portion 90. Thinning tool 92 can be a blade, laser device for ablating material as described for FIG. 7 or FIG. 8, or an abrasive surface that scrapes, sands, or polishes material away. Thinning tool 92 may include a combination of a blade, laser device, and/or abrasive surface to create a smooth finish. Within thinned portion 90, abluminal surface 44 tapers radially inward so that the radial wall thickness of the tubular construct 72 gradually decreases to a point of minimum wall thickness. Thinned portions 90 may be symmetrical as shown in FIG. 14B or they may be non-symmetrical.

As shown in FIG. 14B, tubular construct 72 with thinned portion 90 is processed using cutting tool 76. Cutting tool 76 cuts material away from tubular construct 72 to form a stent scaffold having a plurality of rings 20 connected by link struts 22. A circumferential strip region 96 where an end ring will be cut is registered or aligned within thinned portion 90 so that the end ring will have eased corner feature 42 according to any of FIGS. 9-13.

Figure 15:
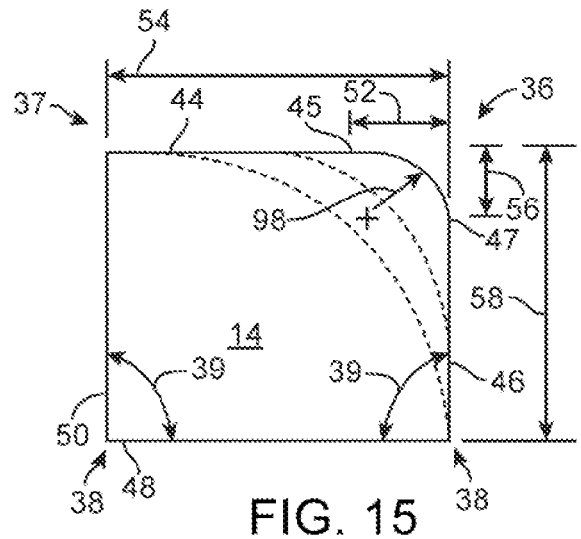
FIG. 15 is a cross-section view of a stent strut, showing a round-type eased corner feature.

In FIG. 15, eased corner feature 42 is in the form of a rounded corner or fillet. This round-type eased corner feature 42 can be substituted for the bevel-type eased corner feature of FIGS. 3-4B to form additional embodiments of the present invention.

As used herein, "round-type eased corner feature" includes one or more curved surfaces, each defined by a convex shape that meets any of strut abluminal surface 44, distal-facing strut side surface 46, or proximal-facing strut side surface 50. The curved surfaces can be smooth or have some irregularities, such as may arise due to incremental laser ablation as described in FIG. 7. For example, strut abluminal surface 44 can meet a first convex surface, and distal-facing strut side surface 46 can meet a second convex surface. Optionally, the first and second convex surfaces can meet. Optionally, an intervening surface is disposed between and meets the first and second convex surfaces.

It will be appreciated that eased corner feature 42 is not limited to the bevel-type and round-type shapes illustrated herein. For example, eased corner feature 42 can be a combination of two or more flat surfaces with a curved surface between two adjacent flat surfaces.

In FIG. 15, round-type eased corner feature 42 is a quarter round. As used herein, a quarter round has a cross-sectional edge that is a quarter circle with opposite ends of the quarter circle being tangent with strut abluminal surface 44 and distal-facing strut side surface 46 (or with proximal-facing strut side surface 50 if implemented on proximal end ring 20*p*, for example).

Round-type eased corner feature 42 can be defined by its radius. In FIG. 15, the solid-line showing of round-type eased corner feature 42 has radius 98 that is 25% of strut width 54. Radius 98 can be at least 5%, at least 10%, at least 25%, at least 50%, at least 75%, or 100% of strut width 54. Eased width 52 and depth 56 of eased corner feature 42 can be as described above for FIG. 5.

The broken lines in FIG. 15 show two non-limiting examples in which eased corner feature 42 is configured with different eased widths 52, different eased depths 56, and different radii 98.

Figure 16:
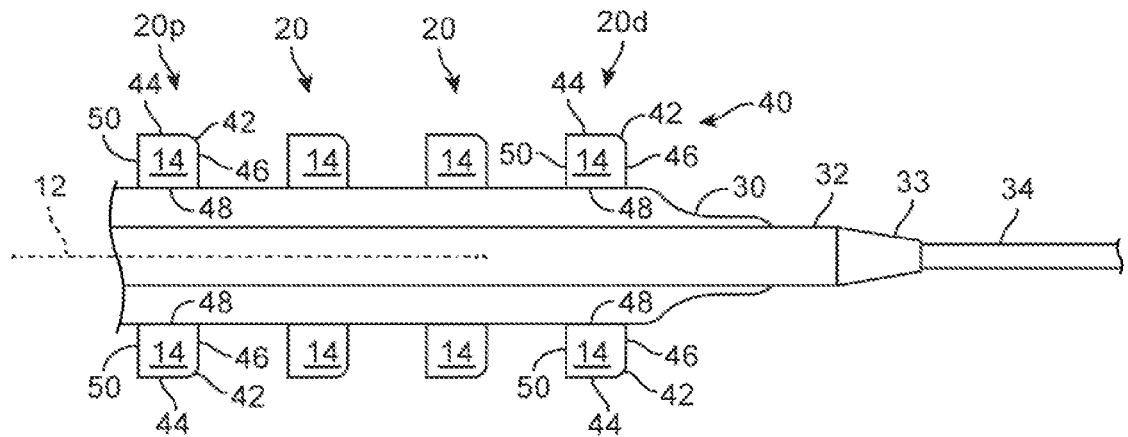
FIG. 16 is a cross-section view of a polymer stent mounted on a catheter, showing an eased corner feature on various rings of the stent.

As shown in FIG. 16, round-type eased corner feature 42 can be present on distal-facing strut side surface 46 on all rings 20, 20p, 20d of stent 40.

Figure 17:
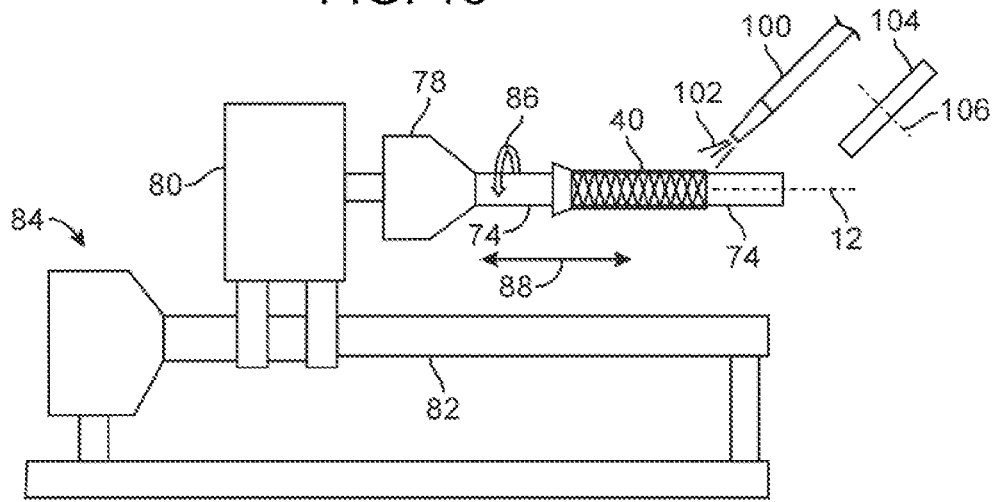
FIG. 17 is an elevation view of an apparatus for fabricating a stent, showing a nozzle for forming an eased corner feature.

As shown in FIG. 17, round-type eased corner feature 42 can be formed by nozzle 100 oriented in a rearward facing direction. For example, a stent scaffold having a plurality of rings 20 connected by link struts 22 can be mounted on mandrel 74 of the apparatus described in FIG. 6. Nozzle 100 is configured to eject abrasive media 102 that removes polymer substrate material from radially outward, distal-facing corners 36 (FIG. 15) to form round-type eased corner feature 42 shown in FIGS. 15 and 16. Mandrel 74 protects strut luminal surfaces 44 so that no polymer substrate material is remove from radially inward corners 38. Round-type eased corner feature 42 can be limited to distal end ring 20d, proximal end ring 20p, or other selected rings 20 by directing the abrasive media only at these rings or by placing a mask or shield over the rings which are not to be exposed to abrasive media 102.

In other embodiments, nozzle 100 is oriented in a forward facing direction to eject abrasive media 102 that removes polymer substrate material from outward, proximal-facing corners 37 to form round-type eased corner feature 42 on proximal-facing strut side surfaces 50 of any one or more of rings 20, 20p, 20d.

Abrasive media include without limitation solid particles of silica, glass, alumina, garnet, sodium bicarbonate, and silicon carbide. The size of the particles can be selected based on strut width and desired width of eased corner feature. An average particle size can be from 1 micron to 25 microns. Embedding of particles of abrasive media into struts can be avoided or minimized through optimization by adjusting any one or more of the size of the particles, velocity of the particles, and material density of the particles. Particles having a material density that is closer to or less than that of the polymer substrate material of stent 40 are expected to be less likely to become embedded than particles having a greater material density. For example, a material density less than 1.25 gm/cm$^3$ may be appropriate for use when the polymer substrate material of the stent comprises poly(L-lactide) ("PLLA").

Abrasive media 102 can be carried by a stream of dry air, nitrogen, or other inert gas, such as argon. After ejection of the abrasive media is completed, the stent can be rinsed with liquid to remove abrasive media on the stent. The liquid can be a solvent of the abrasive media to facilitate removal of any embedded particles of the abrasive media. For example, particles of sodium bicarbonate can be used as the abrasive media, and water can be used to rinse and dissolve away any particles of sodium bicarbonate that might have become embedded in the stent struts.

Alternatively, particles of abrasive media 102 can be carried by a stream of liquid ejected from nozzle 100. The liquid may comprise an aqueous solution or a solvent of the particles.

Round-type eased corner feature 42 can also be formed by directing a spray of liquid which is a partial solvent of the polymer substrate material of stent struts 14. The impact of the spray will deform and soften the polymer substrate material and dissolve away a small amount of the polymer substrate material from radially outward, distal-facing corners to form round-type eased corner feature 42 shown in FIGS. 15 and 16.

Round-type eased corner feature 42 can also be formed by buffing radially outward, distal-facing corners 36 and/or radially outward, proximal-facing corners 37. Buffing can be performed using buffing wheel 104 which rotates about axis 106 and which is coated with abrasive media or fibers. Buffing wheel 104 can be oriented at an oblique angle, similar to the orientation of nozzle 100.

As shown in FIGS. 3-5, 9-10B, 12A, 12B, 16, 15, eased corner feature is absent from all radially inward corners 38 of all rings 20p, 20, 20d of stent 40. For all rings 20p, 20, 20d, strut luminal surface 48 and proximal-facing strut side surface 50 meet to form sharp radially inward corners 38 having an interior angle 39 (FIGS. 5 and 15) of ninety degrees. In other embodiments, sharp radially inward corners 38 have interior angles 39 of less than 100 degrees.

In further embodiments, any of the eased corner feature 42 described above can be implemented on stent 40, such that: (1) eased corner feature 42 is located on radially outward, distal-facing corner 36 but not on radially outward, proximal-facing corner 37 and not on radially inward corners 38; (2) eased corner feature 42 is located on radially outward, proximal-facing corner 37 but not on radially outward, distal-facing corner 36 and not on radially inward corners 38; or (3) eased corner feature 42 is located on radially outward, distal-facing corner 36 and radially outward, proximal-facing corner 37 but not on radially inward corners 38. Case (1), (2), or (3) can be applied to all rings 20p, 20, 20d of stent 40. Case (1), (2), or (3) above can be applied to proximal end ring 20p and distal end ring 20d of stent 40, while all other rings 20 of stent 40 have no eased corner geometry. Case (1), (2), or (3) above can be applied to proximal end ring 20p, while all other rings 20 and 20d of stent 40 have no eased corner geometry. Case (1), (2), or (3) above can be applied to distal end ring 20d, while all other rings 20p and 20 of stent 40 have no eased corner geometry.

In any one or more of the embodiments above, tubular construct 72 (from which stent 40 is made) is a hollow polymer cylinder that has been radially expanded as described in U.S. Pat. No. 8,002,817. The hollow polymer cylinder can be made by extruding one or more bioresorbable polymers through a circular die to form a precursor tube made entirely of the one or more bioresorbable polymers. The precursor tube is then heated and radially expanded, such as by introduction of pressurized air into the tube, in order alter the orientation of molecular polymer chains and thereby increase fracture toughness and strength. Some material is then cut away from the radially expanded tube, such as by laser machining using the apparatus according to any of FIGS. 6, 14A and 14B. The remaining material is in the form of a tubular scaffold comprising various stent struts 14. Eased corner feature 42 can be formed during the laser machining process that forms stent struts 14. Alternatively, eased corner feature 42 can be formed during a secondary process performed after a primary laser machining process that forms stent struts 14.

Figure 18:
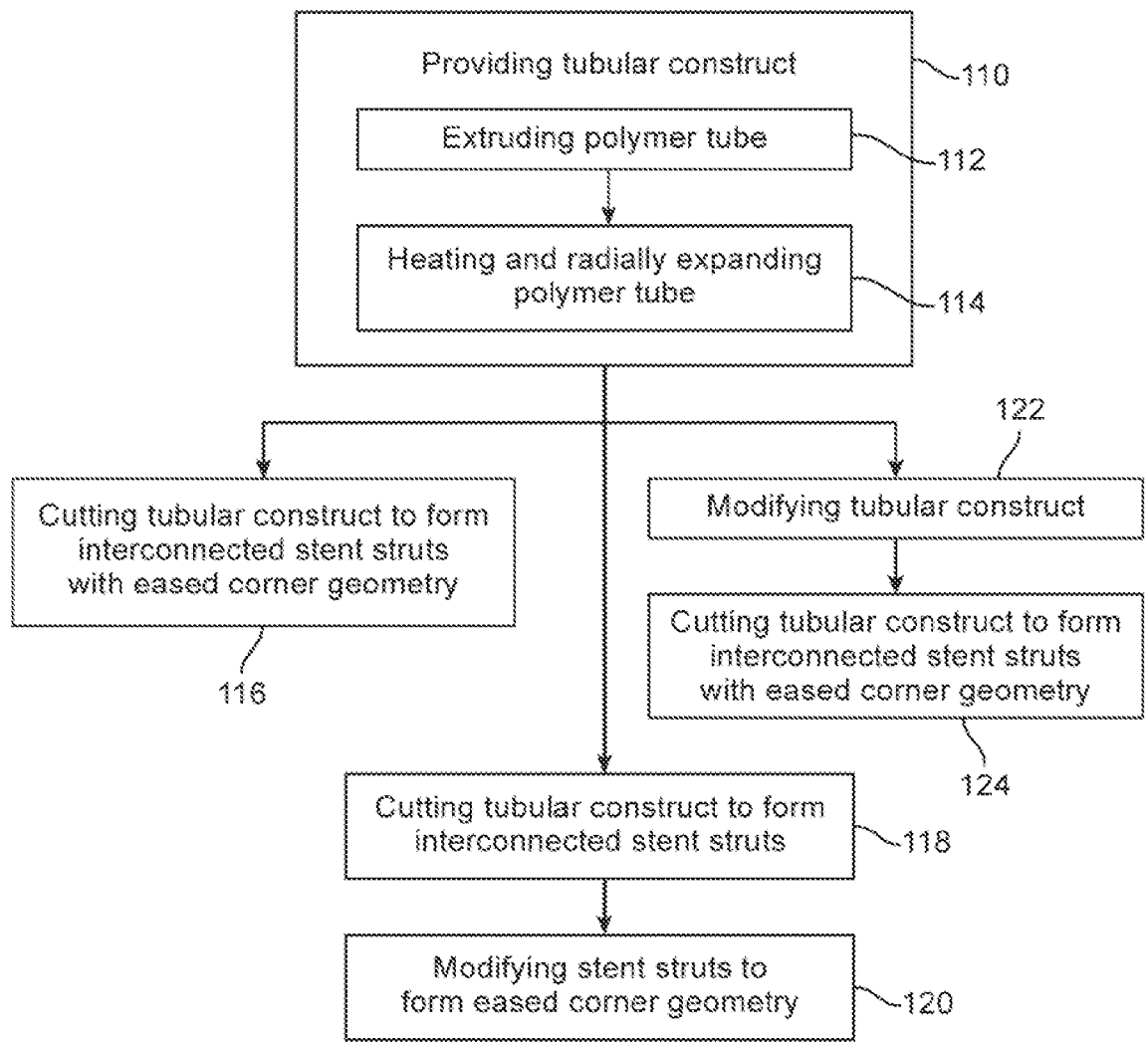
FIG. 18 is a process flow diagram showing methods for fabricating a stent.

A method for fabricating a stent is shown in FIG. 18 with reference to devices described above although the method is not limited to such devices. It will be appreciated that the method can be performed using other types of devices.

In FIG. 18, a method of fabricating a stent includes providing tubular construct 72 in block 110. The tubular construct is made of a polymer substrate material. Block 110 optionally includes extruding a polymer tube in block 112, and optionally followed by heating and radially expanding the extruded polymer tube in block 114. Block 114 may also encompass heating or annealing the polymer tube with no radial expansion of the polymer tube. Alternative methods of providing the tubular construct include dip forming, injection molding polymer material, and rolling a flat sheet of polymer material.

After block 110, the method includes cutting the tubular construct in block 116 to form interconnected stent struts 14 with eased corner feature 42. One or more tools can be used to form stent struts 14 with one or two eased corner features 42. For example, a single cutting tool 76 in any of FIGS. 6-8 can be used to form sharp radially inward corners 38 on struts 14 and to form one or two eased corner features 42 at radially outward corners 36, 37. When forming eased corner feature 42 at one radially outward corner 36 (or 37), sharpness of the other radially outward corner 37 (or 36) and radially inward corners 38 is maintained.

As an alternative to block 116, the method includes cutting tubular construct 72 in block 118 to form stent struts 14. A first tool can be used to form stent struts 14. Stent struts 14 would have sharp radially outward corners 36, 37 and sharp radially inward corners 38. The first tool can be, for example, cutting tool 76 in FIG. 6. After bock 118, the method includes modifying the stent struts in block 120 to form eased corner feature 42 to remove sharpness at any of radially outward corners 36, 37. Modification of stent struts 14 includes removing or softening polymer substrate material at any of radially outward corners 36, 37. When modify stent struts 14 to have eased corner feature 42 at one radially outward corner 36 (or 37), sharpness is maintained at the other radially outward corner 37 (or 36) and at radially inward corners 38. A second tool can be used to modify stent struts 14. The second tool can be any one or a combination of cutting tool 76 in FIGS. 7 and 8, nozzle 100 in FIG. 17, and buffing wheel 104 in FIG. 17.

As an alternative to blocks 116-120, the method includes modifying tubular construct 72 in block 122 to have a non-uniform wall thickness. For example, thinning tool 92, such as shown in FIG. 14A, can be used to remove material from abluminal surface 44 of tubular construct 72. Thinning tool 92 removes polymer substrate material without penetrating entirely through tubular construct 72. After block 122, the method includes cutting the tubular construct in block 124 to form interconnected stent struts 14 with eased corner feature 42. Eased corner feature 42 is present as soon as cutting tool penetrates entirely through tubular construct 72 to form proximal-facing side surfaces 50 and distal-facing side surfaces 46. That is, eased corner feature 42 is formed using a combination of the thinning tool followed by the cutting tool. For example, cutting tool 76, such as shown in FIG. 14B, can be used. When cutting side surfaces 46, 50 into thinned portion 90 of tubular construct 72, cutting tool 76 forms sharp radially inward corners 38 and forms eased corner feature 42. Cutting thinned portion 90 results in formation of eased corner feature 42 while sharpness is maintained at radially inward corners 38 and at one of the radially outward corners 37, 36.

In the embodiments above, stent 40 is made of a polymer substrate material. The polymer substrate material can be a biostable polymer substrate material or a bioresorbable polymer substrate material. In any one or more embodiments above, the bioabsorbable polymer material is a material selected from the group consisting of poly(L-lactide) ("PLLA"), poly(L-lactide-co-glycolide) ("PLGA"), poly(D, L-lactide-co-glycolide), poly(L-lactide-co-caprolactone), poly(glycolide-co-caprolactone) and poly(L-lactide-co-D-lactide) ("PLLA-co-PDLA"). Examples of polymers for the polymer substrate material include without limitation the polymers described in U.S. Pat. No. 8,002,817.

A surface coating containing a therapeutic agent, a polymer, solvent, or a combination thereof, can be applied on the polymer substrate material. The surface coating is not a substrate material of stent 40. Therapeutic agents include without limitation drugs and substances that, when administered in therapeutically effective amounts, have a therapeutic beneficial effect on the health and well-being of the patient or subject. Therapeutic agents include without limitation an anti-proliferative, anti-inflammatory or immune modulating, anti-migratory, anti-thrombotic or other pro-healing agent or a combination of two or more thereof. Therapeutic agents include without limitation those described in U.S. Publication Nos. 2010/0244305. Polymers include without limitation those described in U.S. Pat. No. 8,002,817.

Eased corner feature 42 can be implemented on polymer stent rings of various shapes, such as rings disclosed in U.S. Pat. Nos. 8,002,817, 8,303,644, 8,388,673, and 8,323,760, and in U.S. Publication Nos. 2010/0244305 and 2013/0085563. For example, stent rings can have a sinusoidal shape, as shown in FIGS. 4A, 10A and 12A. The sinusoidal shape is formed by an axially undulating arrangement of ring struts joined together by bending elements. The sinusoidal shape includes a series of repeating S-curves. In FIGS. 4A, 10A, and 12A, an S-curve is formed by first link strut 16 at the top of the figure, which is connected by distal bending element 18b to second link strut 16, which is connected by proximal bending element 18a to third link strut 16. Stent rings need not be sinusoidal or undulating. For example, a stent ring can have the shape of a cylindrical band such as ring member 40 in FIG. 3 of U.S. Publication No. 2010/0244305.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. An implantable stent comprising:
a first ring and a second ring, each of the first ring and the second ring made of a polymer substrate material forming a strut abluminal surface, a strut luminal surface, a distal-facing strut side surface, and a proximal-facing strut side surface,
wherein the distal-facing strut side surfaces are normal to and meet strut luminal surfaces to form radially inward corners not dulled or blunted on the first ring and the second ring, a corner feature is formed in the polymer substrate material of the first ring, and the corner feature is located at a radially outward, distal-facing corner of the first ring and, wherein the corner feature blunts or dulls the radially outward, distal facing corner and is defined by a surface between the strut abluminal surface and the distal-facing strut side surface, and wherein the surface defining the corner feature has a step-wise profile.

2. The implantable stent of claim 1, wherein the corner feature has a corner feature width and a corner feature depth, the corner feature width is at least 5% of strut width, and the corner feature depth is at least 5% of strut height.

3. The implantable stent of claim 1, wherein the first ring is a distal end ring.

4. The implantable stent of claim 1, wherein a corner feature is formed in the polymer substrate material of the second ring and defined by a surface having a step-wise profile.

5. The implantable stent of claim 4, wherein the corner feature of the second ring is located on a radially-outward, distal-facing corner of the second ring.

6. The implantable stent of claim 4, wherein the corner feature of the second ring is located on a radially-outward, proximal-facing corner of the second ring.

7. The implantable stent of claim 6, wherein the first ring is a distal end ring, and second ring is a proximal end ring.

8. The implantable stent of claim 1, further comprising a plurality of additional rings each of which made of the polymer substrate material, wherein a corner feature is formed in the polymer substrate material at radially outward, distal-facing corner of each of the additional rings, and the corner feature is defined by a surface having a step-wise profile.

9. The implantable stent of claim 1, wherein the first ring includes ring struts joined together by a proximal bending element and a distal bending element, wherein the ring struts, the proximal bending element, and the distal bending element form a sinusoidal shape, wherein a width ratio is a ratio of corner feature width of the corner feature to strut width, and the width ratio of the first ring is the same at the proximal bending element and at the distal bending element, and a corner feature depth of the corner feature of the first ring is the same at the proximal bending element and at the distal bending element.

10. The implantable stent of claim 9, wherein the corner feature width at the proximal bending element and at the distal bending element is less than 100% of strut width.

11. The implantable stent of claim 9, wherein the corner feature width at the proximal bending element and at the distal bending element is 100% of strut width.

12. The implantable stent of claim 1, wherein the step-wise profile includes a plurality of steps, and each step defined by having an elevation different from that of an adjacent one of the steps.

13. The implantable stent of claim 12, wherein each step is formed by a laser pulse directed perpendicular to the strut abluminal surface.

14. The implantable stent of claim 1, wherein the radially inward corners have no beveled or rounded edge.

* * * * *